United States Patent
Badawy

(10) Patent No.: US 10,765,599 B2
(45) Date of Patent: Sep. 8, 2020

(54) DEVICE FOR REDUCING MEDICATION NON-ADHERENCE

(71) Applicant: Sherif Badawy, Chicago, IL (US)

(72) Inventor: Sherif Badawy, Chicago, IL (US)

(73) Assignee: Sherif Badawy, Chicago, IL (US)

( * ) Notice: Subject to any disclaimer, the term of this patent is extended or adjusted under 35 U.S.C. 154(b) by 32 days.

(21) Appl. No.: 15/875,814

(22) Filed: Jan. 19, 2018

(65) Prior Publication Data

US 2019/0224072 A1    Jul. 25, 2019

(51) Int. Cl.
| | |
|---|---|
| *A61J 1/03* | (2006.01) |
| *B65D 81/36* | (2006.01) |
| *B65D 21/02* | (2006.01) |
| *B65D 77/04* | (2006.01) |
| *A61J 7/04* | (2006.01) |

(52) U.S. Cl.
CPC ............ *A61J 1/03* (2013.01); *B65D 21/0233* (2013.01); *B65D 77/04* (2013.01); *B65D 77/0486* (2013.01); *B65D 81/365* (2013.01); *A61J 7/04* (2013.01); *A61M 2205/59* (2013.01); *B65D 2583/0445* (2013.01); *B65D 2583/0463* (2013.01)

(58) Field of Classification Search
CPC .. A61J 1/03; A61J 7/04; B65D 81/365; B65D 77/0486; B65D 77/04; B65D 2583/0463; A61M 2205/59
USPC ................................................ 206/528, 457
See application file for complete search history.

(56) References Cited

U.S. PATENT DOCUMENTS 2,845,065 A * 7/1958 Gabriel ................. A61M 5/425
                                                                  604/198
3,299,891 A * 1/1967 Smeton ............... A61M 5/3129
                                                                  604/232
(Continued)

FOREIGN PATENT DOCUMENTS

| CN | 201530150734.3 | 5/2015 |
| CN | 201530274886.4 | 7/2015 |

(Continued)

OTHER PUBLICATIONS

Various images of products.
(Continued)

*Primary Examiner* — Steven A. Reynolds
(74) *Attorney, Agent, or Firm* — Beem Patent Law Firm

(57) ABSTRACT

A decorative medication holder may reduce or eliminate medication non-adherence and work with standard and/or non-standard medication containers. The medication holder may include a body portion having an opening to a medication retaining cavity adapted for receiving a medication, such as a bottle of pills. The body portion also may be decorated with a kid-friendly aesthetic design, such as a character, animal, or the like to engage a child's interest. In some embodiments, the body portion may include a substantially flat outer surface. Alternatively, the body portion also may include three-dimensional limbs or the like which may be rigid or posable. In some embodiments, a cover may be provided to close the opening and/or secure the medication in the cavity. Alternatively, or additionally, the cavity may include textured lining or the like to grip the medication in the cavity. Other embodiments also are described.

17 Claims, 6 Drawing Sheets

(56) References Cited

U.S. PATENT DOCUMENTS

| | | | | |
|---|---|---|---|---|
| 4,708,254 | A * | 11/1987 | Byrns | B65D 23/0857 |
| | | | | 215/13.1 |
| D327,128 | S * | 6/1992 | Nightingale | D24/198 |
| 5,386,909 | A * | 2/1995 | Spector | B65D 77/04 |
| | | | | 206/457 |
| 5,487,750 | A * | 1/1996 | Burchett | A61J 7/0046 |
| | | | | 222/133 |
| 5,871,184 | A * | 2/1999 | Kaopio | A61J 9/08 |
| | | | | 248/102 |
| 6,237,787 | B1 * | 5/2001 | Gallo | A63H 3/005 |
| | | | | 206/457 |
| 6,626,326 | B2 * | 9/2003 | Murakami | B65D 81/3881 |
| | | | | 220/23.87 |
| 6,641,094 | B2 * | 11/2003 | Fishler | A61J 9/08 |
| | | | | 248/102 |
| 6,824,112 | B2 * | 11/2004 | Lange | A61J 9/0607 |
| | | | | 248/102 |
| 7,908,683 | B1 | 3/2011 | Finell | |
| 8,123,055 | B2 * | 2/2012 | Loving | A47J 41/0077 |
| | | | | 206/457 |
| 9,340,323 | B1 * | 5/2016 | Tate | B65D 23/001 |
| 2009/0152159 | A1 * | 6/2009 | Beeman | A45C 11/00 |
| | | | | 206/570 |
| 2012/0061286 | A1 * | 3/2012 | Hueb De Menezes Oliveira | A61B 5/150389 |
| | | | | 206/571 |
| 2013/0087572 | A1 * | 4/2013 | Dinges | B65D 81/3876 |
| | | | | 220/737 |
| 2014/0175105 | A1 * | 6/2014 | Martin | A47G 23/0233 |
| | | | | 220/739 |
| 2014/0291182 | A1 * | 10/2014 | Cascio | A45F 5/02 |
| | | | | 206/389 |

FOREIGN PATENT DOCUMENTS

| | | |
|---|---|---|
| FR | DM081083 | 5/2013 |
| FR | DM089018 | 8/2015 |
| WO | 9620768 A1 | 7/1996 |

OTHER PUBLICATIONS

Ebay Listing of Minion Toothpaste Dispenser. https://www.ebay.com/itm/Minion-Toothpaste-Dispenser-Minion-One-Eye-Minion-Stickers-Enclosed/133008922679?hash=item1ef7f31837:g:fm0AAOSw2EJcoVht. First accessed May 29, 2019.

* cited by examiner

DEVICE FOR REDUCING MEDICATION NON-ADHERENCE

BACKGROUND OF THE INVENTION

1. Technical Field

The present application relates to devices for reducing medication non-adherence, and particularly medication non-adherence in children with chronic medical conditions.

2. Related Art

In 2010, the United States spent $2.6 trillion on health care, about 18% of its gross domestic product. Continued rising health care costs despite the recession, the increasing US national deficit, and the increasing percentage of US health spending financed by the government ($1.2 trillion, 45% of all US health spending) have prompted investigation of modifiable factors to reduce health care use and associated costs. According to some researchers, about 83% of health care resources are consumed by individuals who have chronic medical conditions.

The number of children and adolescents diagnosed with a chronic medical condition has been steadily increasing over the past 20 years, driven in part by increases in the prevalence of obesity and asthma as well as advances in medical care that increase survival from serious medical conditions (e.g., cystic fibrosis, kidney transplant). Increases in the prevalence of chronic medical conditions have only increased the already disproportionate health care expenses accounted for by children and adolescents who have a chronic illness. In 2000, children and adolescents with a special health care need made up 16% of all youth in America but accounted for 53% of hospital days. Consequently, this population provides one of the greatest opportunities to reduce pediatric health care spending.

Non-adherence refers to a lack of correspondence between patient self-management behavior and medical or health advice and significantly contributes to health care use in adults who have a chronic illness, accounting for an estimated 33% to 69% of adult hospital admissions and $100 to $300 billion in annual health care costs. Because much of the health care use attributable to non-adherence includes excess use of urgent care and hospitalizations for preventable complications, it represents avoidable costs, an ideal target outcome for interventions aimed at reducing health care spending. As non-adherence is modifiable with intervention, adult adherence promotion efforts have begun to focus on both improving health status and reducing health care use, resulting in programs that effectively decrease health care costs.

While much has been done to increase adherence among adults, similar efforts to contain pediatric health care costs have not yet been examined despite the widespread nature of non-adherence in pediatrics. Approximately 63% of children and adolescents who have a chronic illness are prescribed medication, but 50% to 88% of children and adolescents are non-adherent to their prescribed regimens. As in adult samples, pediatric non-adherence may be a modifiable predictor of health care use and resulting health care costs. For example, an adolescent who has asthma may require hospitalization after failing to take his controller medication for several days and suffering an exacerbation. This hospitalization and its associated costs may have been avoided.

Understanding the impact of adherence promotion interventions on health care costs specific to pediatric populations is necessary given the numerous developmental factors that make pediatric adherence unique. These factors include, for example, the influence of adult caregivers and systems on adherence, the evolution of illness burden with age, increasing autonomy for disease management, and the like. In addition, the variations in health care systems and outcomes across a patient's lifespan also contribute to adherence rates. For example, health care financing for over one-third of children and adolescents is provided by Medicaid and Children's Health Insurance Programs. However, given the more advanced disease course and higher likelihood of complications experienced by adults who have a chronic illness, the benefits in quality of life and cost savings resulting from pediatric prevention efforts, while likely to be less visible in short-term evaluations, may provide substantial long-term savings because long-term self-management behaviors are often developed in childhood and adolescence. Specifically, promoting adherence in pediatric populations may have the potential to reduce short-term health care use as well as long-term health care use that may result from the increased morbidity associated with non-adherence.

Accordingly, a need has long existed for devices that reduce medication non-adherence.

SUMMARY

In one embodiment, a decorative medication holder may reduce or eliminate medication non-adherence and work with standard and/or non-standard medication containers. The medication holder may include a body portion having an opening to a medication retaining cavity adapted for receiving a medication, such as a bottle of pills. The body portion also may be decorated with a kid-friendly aesthetic design, such as a character, animal, or the like to engage a child's interest. In some embodiments, the body portion may include a substantially flat outer surface. Alternatively, the body portion also may include three-dimensional limbs or the like which may be rigid and/or posable. In some embodiments, a cover may be provided to close the opening and/or secure the medication in the cavity. Alternatively, or additionally, the cavity may include textured lining or the like to grip the medication in the cavity. Other embodiments also are described.

Other systems, methods, features and advantages of the invention will be, or will become apparent to one with skill in the art upon examination of the following figures and detailed description. It is intended that all such additional systems, methods, features and technical advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION OF THE PREFERRED EMBODIMENTS

The elements illustrated in the Figures interoperate as explained in more detail below. Before setting forth the detailed explanation, however, it is noted that all of the discussion below, regardless of the particular implementation being described, is exemplary in nature, rather than limiting.

1.0 Medication Accessory Overview

Figure 2:
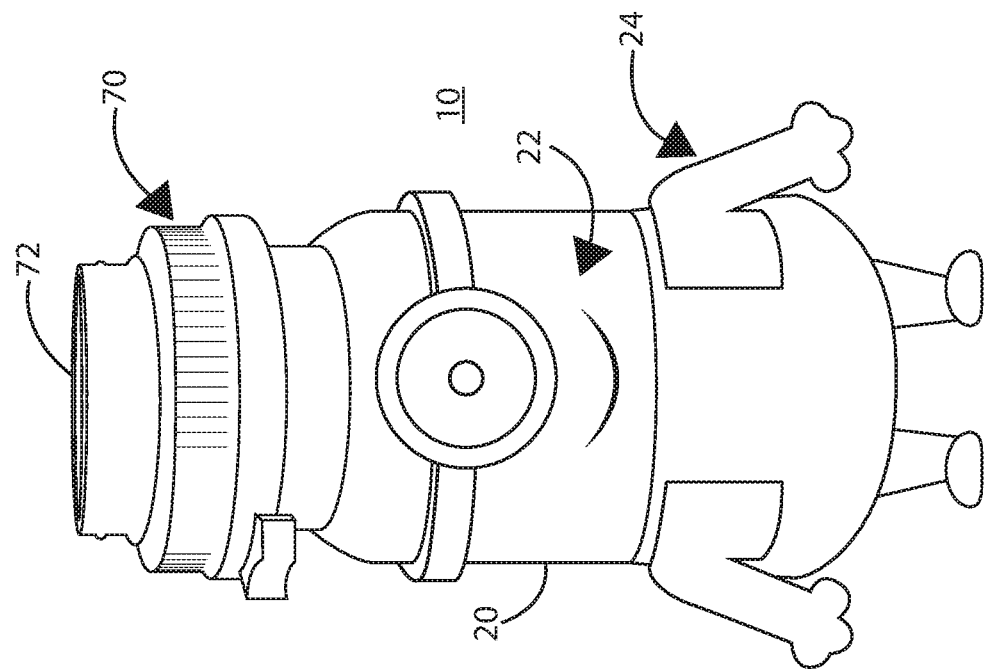
FIG. 2 shows a perspective view of the exemplary medication accessory of FIG. 1 with an exemplary bottle of pills.
Figure 1:
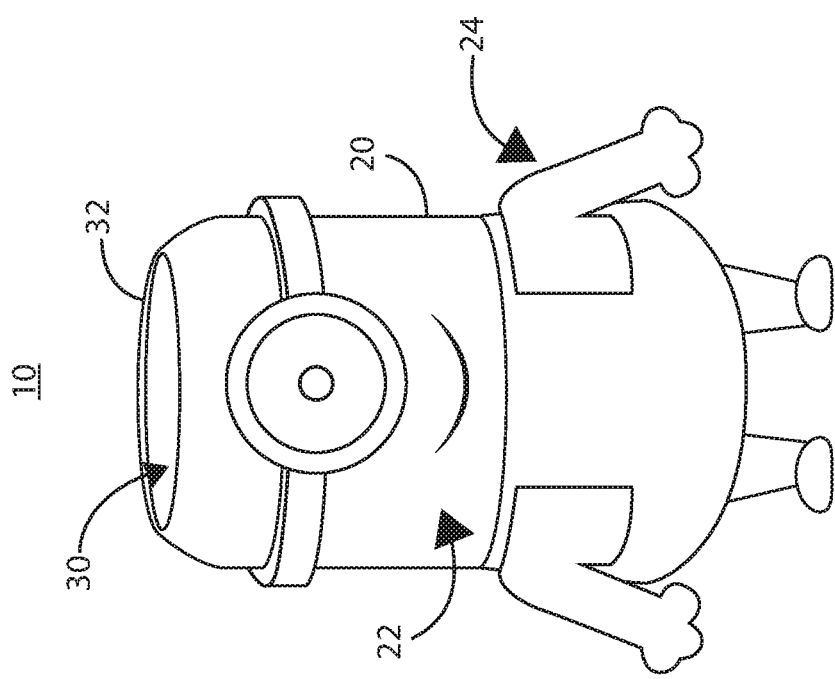
FIG. 1 shows a perspective view of an exemplary medication accessory for reducing medication non-adherence.
Figure 4:
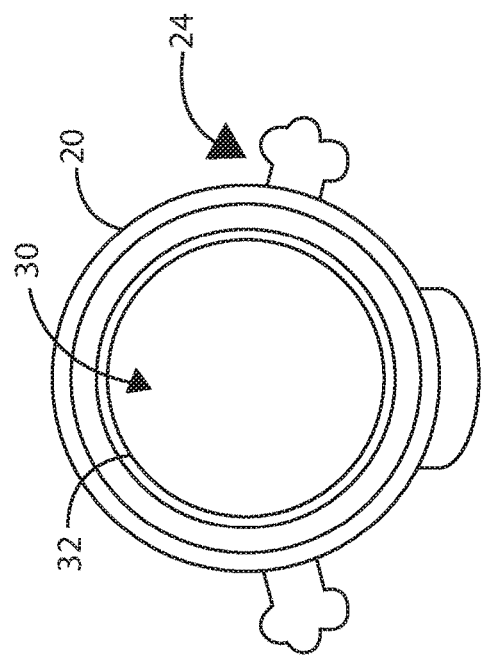
FIG. 4 shows a top view of the exemplary medication accessory of FIG. 2.

Referring to the drawings and initially to FIGS. 1 and 2, perspective views of an exemplary medication accessory for reducing medication non-adherence 10 are shown. The accessory 10 may include a medication retaining cavity 30 that is adapted to hold a medication 70, such as a bottle of pills as shown in FIG. 2. In addition, the accessory 10 may include a body 20 having an aesthetic design 22 that is engaging for the patient. In the illustrated embodiment, the aesthetic design 22 is one of a MINION character from the movie MINIONS produced by Illumination Entertainment for Universal Pictures. In some embodiments, such as the embodiment shown in FIG. 1, the accessory 10 may include external features 24 that extend outward from the body, such as limbs, clothing, and the like.

In operation, a medication 70 may be placed into the medication retaining cavity 30 and thereafter be accessible for use as prescribed. As used herein, the phrase "medication retaining cavity" means a cavity that is adapted to receive a medication container, such as a bottle of pills or the like, and retain or hold the medication container in place. In other words, the phrase "medication retaining cavity" means that the medication is retained tightly in the cavity, allowing some movement while keeping the medication in a relatively fixed position in which the medication is accessible. For example, in the embodiment illustrated in FIG. 2, the medication substantially fills the cavity and remains in an upright position in which the cap is accessible and may be removed and/or attached to the bottle while the bottle is retained in the cavity.

2.0 Exemplary Body Portions 20

The body portion 20 may be dimensioned to correspond to typical medication bottle sizes. For example, the body portion 20 may be dimensioned to receive pill bottles 70 in the cavity 30. Pill bottles 70 come in variety of sizes, typically measured in drams. For example, a typical 6 dram pill bottle 70 may be a cylindrical bottle having a diameter of about 2 centimeters (cm) and a height (including the cap) of about 6.5 cm, a typical 8 dram pill bottle 70 may be a cylindrical bottle having a diameter of about 2.5 cm and a height (including the cap) of about 7 cm, a typical 13 dram pill bottle 70 may be a cylindrical bottle having a diameter of about 3 cm and a height (including the cap) of about 6.7 cm, a typical 16 dram pill bottle 70 may be a cylindrical bottle having a diameter of about 3 cm and a height (including the cap) of about 8 cm, a typical 20 dram pill bottle 70 may be a cylindrical bottle having a diameter of about 3.5 cm and a height (including the cap) of about 6 cm, a typical 30 dram pill bottle 70 may be a cylindrical bottle having a diameter of about 3.5 cm and a height (including the cap) of about 9 cm, and a typical 40 dram pill bottle 70 may be a cylindrical bottle having a diameter of about 4.3 cm and a height (including the cap) of about 9 cm.

Accordingly, an accessory 10 for holding a 6 dram bottle having the dimensions above may include an opening 32 having a diameter between about 2.01 cm and about 2.5 cm, preferably between about 2.02 and about 2.3 cm, and even more preferably between about 2.05 cm and about 2.1 cm. Similarly, an accessory 10 for holding a 6 dram bottle having the dimensions above may include a depth of the medication retaining cavity 30 between about 5.5 cm and about 6.4 cm, preferably between about 5.7 cm and about 6.3 cm and even more preferably between about 5.8 cm and about 6.2 cm.

In some embodiments, the dimensions of the accessory 10 may be proportional to the size of the medication bottle. For example, a diameter of the opening 32 may by between about 100.5% and about 125% of the diameter of the medication 70, preferably between about 101% and about 115% of the diameter of the medication 70, even more preferably between about 102% and about 110% of the diameter of the medication 70, and even more preferably between about 102.5% and about 105% of the diameter of the medication 70. Similarly, the depth of the medication retaining cavity 30 may be between about 75% and about 99% of the length of the medication 70, preferably between about 80% and about 95% of the length of the medication 70, and even more preferably between about 85% and about 90% of the length of the medication 70. In some embodiments, the depth of the medication retaining cavity 30 may be dimensioned so an upper portion of the medication, such as the cap, a lock/release mechanism (e.g. childproof lock mechanism) (as shown in FIG. 2) or other protrusion that extends beyond the main body of the medication container 70, abuts the opening 32 when the medication container 70 is disposed in the medication retaining cavity 30.

Body portion 20 may be made of plastic (such as acrylic), rubber, metal, stone, wood or any other suitable material that may provide durability to absorb forces that may be encountered during use, such as, for example, by a child. Any other suitable material also may be used. Body portion 20 may be a single piece, or multiple pieces may be used that connect to one another, the medication container, or both. For example, an accessory 10 may be provided with an aesthetic design 22 resembling a baseball player having a helmet that is attachable to the cap of a medication container.

Figure 7:
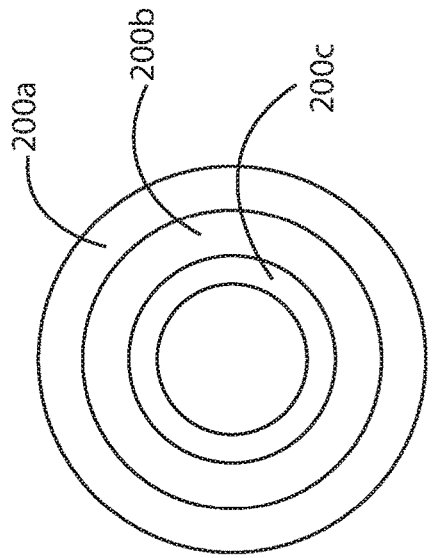
FIG. 7 shows a top view of a nested set of exemplary medication accessories for reducing medication non-adherence.
Figure 3:
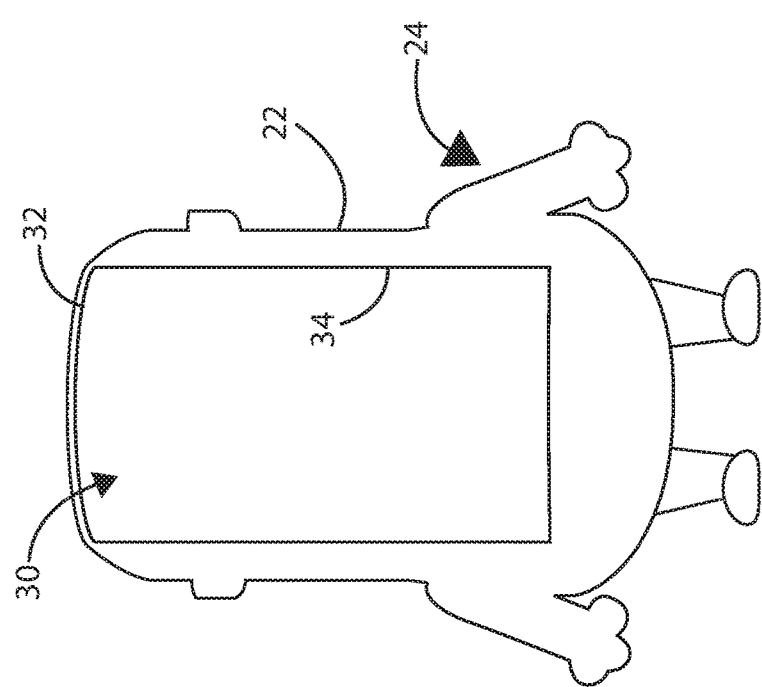
FIG. 3 shows a side cutaway view of an exemplary pocket of the exemplary medication accessory shown in FIG. 1.
Figure 6:
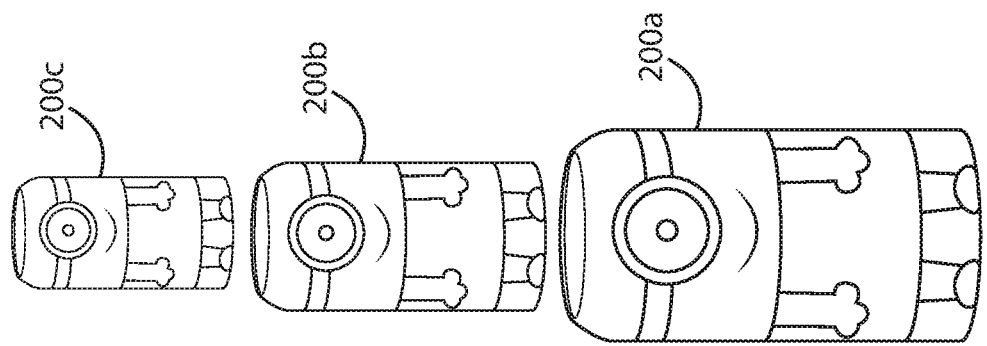
FIG. 6 shows an exploded view of a set of exemplary medication accessories for reducing medication non-adherence that may be nested.
Figure 5:
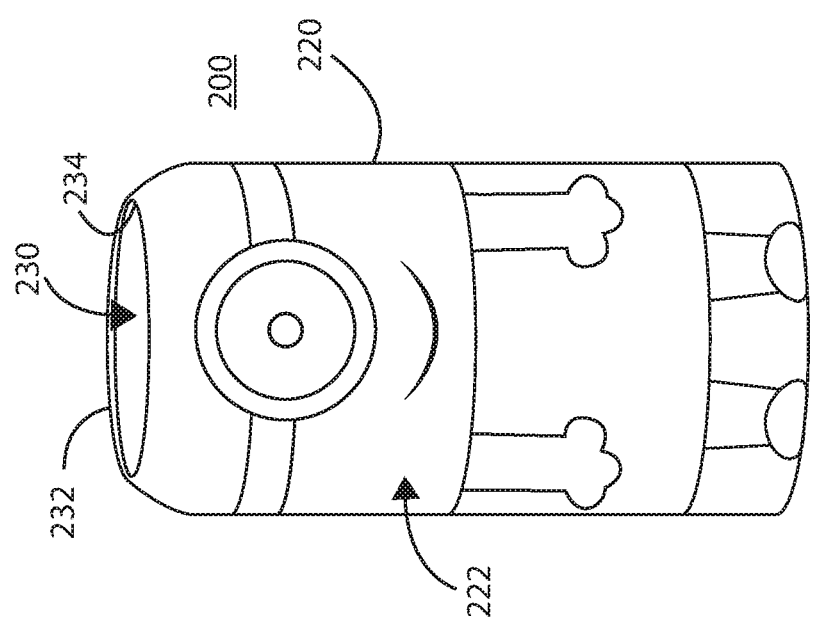
FIG. 5 shows a perspective view of another exemplary medication accessory for reducing medication non-adherence.

In some embodiments, such as the embodiments depicted in FIGS. 1-4 and 8, the body 20 may include three dimensional components 24. These three-dimensional components may be provided to more accurately depict the aesthetic design of the character, as described more fully below. In other embodiments, such as the embodiments depicted in FIGS. 5-7 and 9, the accessories 200 may include substantially flat outer surfaces 225. By using substantially flat outer surfaces 225, sets of accessories 200a, 200b and 200c may be provided to accommodate bottles 70 of various sizes. In some embodiments, sets of accessories 200a, 200b and 200c may be provided in a nested fashion where an accessory 200a for retaining a smaller sized bottle may fit within an accessory 200b for retaining a medium sized bottle, and that accessory also may fit within an accessory 200c for retaining a large bottle. Exemplary nested sets of accessories 200a, 200b and 200c are shown in FIG. 6 in an exploded view and in FIG. 7 from a top down perspective.

2.1 Exemplary Aesthetic Designs

The aesthetic design 22 may be chosen to increase compliance with for a specific target patient. For example, the use of a kid-friendly aesthetic design 22 may increase compliance with the prescribed medication protocol with children. Exemplary kid-friendly aesthetic designs may include animal designs, occupational designs, character designs, and the like. For example, animal designs may include aesthetic designs 22 that resemble dogs, cats, horses, pigs, sheep, mice, birds, insects, dinosaurs, fish, and the like. Exemplary occupational designs may include aesthetic designs that resemble doctors, nurses, lawyers, scientists, engineers, athletes, teachers, police, firefighters, emergency medical technicians, race car drivers, pilots, chefs, and the like.

Character designs may include characters from television shows and movies such as characters from ANNA or ELSA from FROZEN, MICKEY MOUSE, MINNIE MOUSE, WINNIE THE POOH or the like provided by THE WALT DISNEY COMPANY of Burbank, Calif., DORA THE EXPLORER and SPONGEBOB SQUAREPANTS provided by NIKELODEON of New York, N.Y., any of the POKEMAN characters provided by NINTENDO of Kyoto, Japan, super-heroes such as BATMAN or SUPERMAN provided by DC COMICS of Burbank, Calif., TRANSFORMER characters provided by HASBRO of Pawtucket, R.I. and the like. Other designs 22 also may be used.

As noted above, in some embodiments, such as the embodiments depicted in FIGS. 1-4 and 8, the body 20 may include three dimensional components 24. These three-dimensional components may be provided to more accurately depict the aesthetic design 22 of the accessory 10. For example, accessories 10 having an animal aesthetic 22 may have three-dimensional components 24 such as limbs, such as arms, legs, paws, tails, ears, fur, and the like. Similarly, accessories having a character or occupational aesthetic 22 may include three-dimensional components 24 such as limbs like arms, legs, hands, feet and the like. Other portions of the body 20 of the accessory 10 may be provided three-dimensionally. The three-dimensional components 24.

2.2 Exemplary Features for Enabling Viewing of Prescription Labels

In some embodiments, features may be provided that enable a patient to view at least a portion of the prescription label 74 when the prescription is disposed in the medication retaining cavity 30. These features may allow a user to verify the medication disposed in the accessory 10, view dosage instructions, confirm refill availability, see how many pills may be remaining and the like. For example, in the embodiment shown in FIG. 8, an accessory 100 is provided with a body 120 having an aperture 124 that enables a patient to view a portion of the prescription label 74. In the illustrated embodiment, the aperture 124 is provided as a longitudinal hole in the body 120 that exposes a portion of the prescription label on a pill bottle 70. To read additional information, the patient may spin the bottle within the cavity 130, thereby exposing different portions of the label 74.

Various dimensioned apertures 124 may be used. For example, in the embodiment illustrated in FIG. 8, the aperture 124 is a substantially longitudinal rectangle that is substantially vertically disposed. A longitudinal, vertically disposed aperture 124 may allow a patient to read a label over a larger cross section of the bottle 70, reducing issues that may be caused by inconsistent label 74 placement. Alternatively, or additionally, horizontally disposed apertures 124 may be provided. In some embodiments, multiple apertures 124 may be provided. Other shapes also may be used for apertures 124, such as squares, circles, and the like. In some embodiments, the aperture 124 may be dimensioned to have a length between about 30% and about 70% of the length of the body portion 20, preferably between about 40% and about 60% of the length of the body portion 20, and even more preferably between about 45% and about 55% of the length of the body portion 20. Similarly, the width of the aperture 124 may be dimensioned to be between about 10% and about 50% of the width of the body portion 20, preferably between about 15% and about 35% of the width of the body portion 20, even more preferably between about 20% and about 30% of the width of the body portion 20. In a particular embodiment, the length of the aperture 124 may be about 50% of the length of the body portion 20 and the width of the aperture 124 may be about 25% of the width of the body portion 20.

Figure 9:
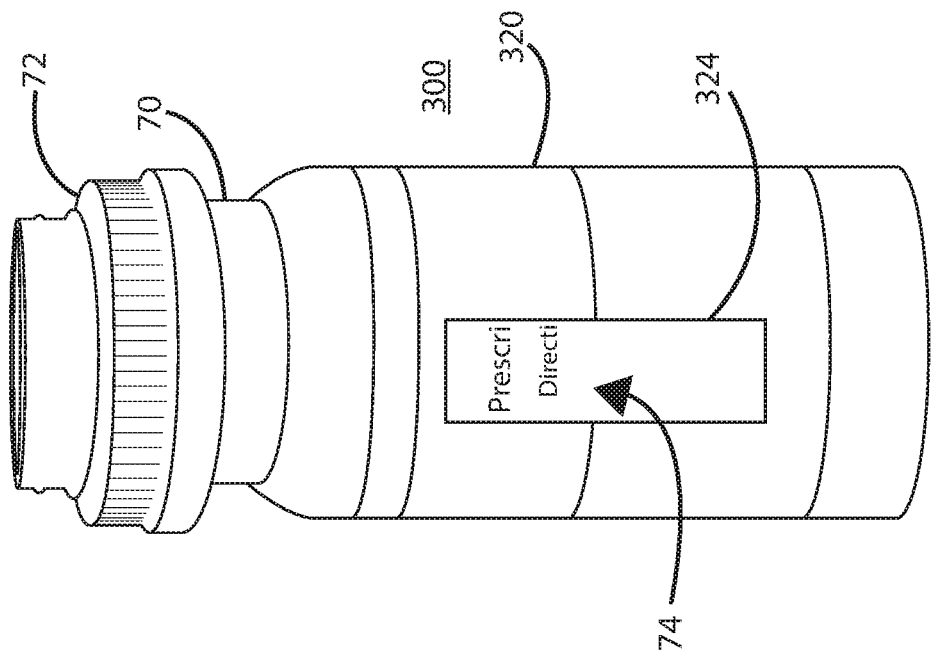
FIG. 9 shows a back view of another exemplary medication accessory for reducing medication non-adherence.
Figure 8:
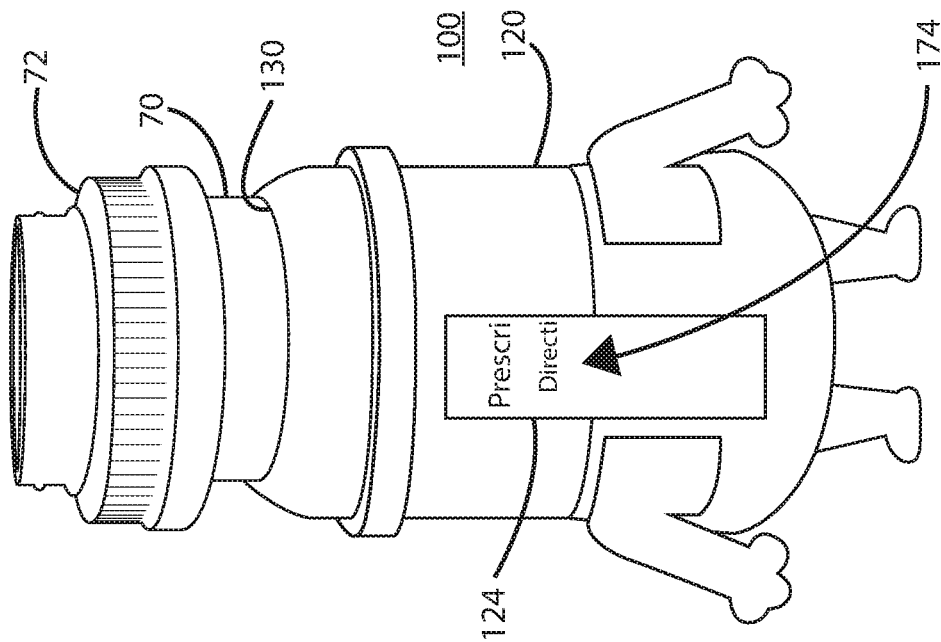
FIG. 8 shows a back view of another exemplary medication accessory for reducing medication non-adherence.

Alternatively, or additionally, portions of the body 20 may be transparent to enable a patient to view at least a portion of the prescription label 74 when the prescription is disposed in the medication retaining cavity 30. An exemplary accessory 300 having a transparent portion 324 of the body 320 is shown FIG. 9. Similar to the aperture 124 described above in reference to FIG. 8, the transparent portion 324 shown in the embodiment illustrated in FIG. 9 is a substantially longitudinal rectangle that is substantially vertically disposed. Again, a longitudinal, vertically disposed transparent portion 324 may allow a patient to read a label over a larger cross section of the bottle 70, reducing issues that may be caused by inconsistent label 74 placement. In some embodiments, the transparent portion 324 may be dimensioned to have a length between about 30% and about 70% of the length of the body portion 20, preferably between about 40% and about 60% of the length of the body portion 20, and even more preferably between about 45% and about 55% of the length of the body portion 20. Similarly, the width of the transparent portion 324 may be dimensioned to be between about 10% and about 50% of the width of the body portion 20, preferably between about 15% and about 35% of the width of the body portion 20, even more preferably between about 20% and about 30% of the width of the body portion 20. In a particular embodiment, the length of the transparent portion 324 may be about 50% of the length of the body portion 20 and the width of the transparent portion 324 may be about 25% of the width of the body portion 20.

Similar to apertures 124, transparent portions 324 may be horizontally disposed, and may be provided in a variety of shapes, such as squares, circles, and the like. In some embodiments, a substantial portion or all of the body 320 may be transparent. For example, the portion of the body 20 corresponding to the character's skin may be transparent.

3.0 Exemplary Embodiments For Holding Other Medications

Figure 11:
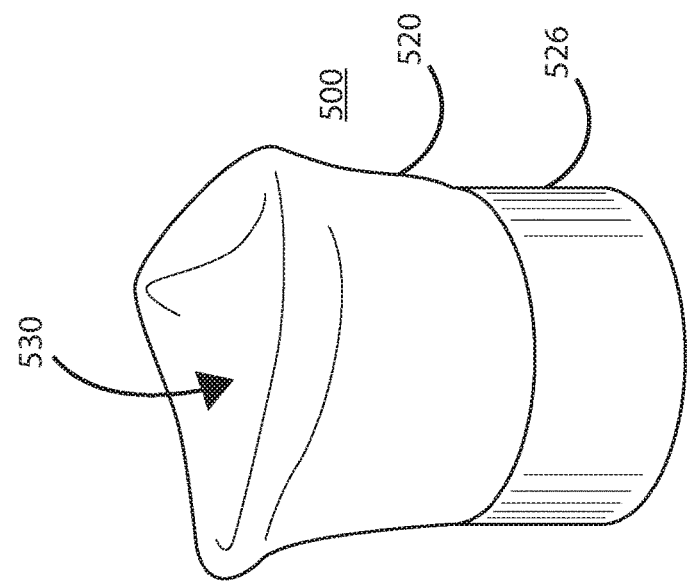
FIG. 11 shows a perspective view of another exemplary medication accessory for reducing medication non-adherence.
Figure 10B:
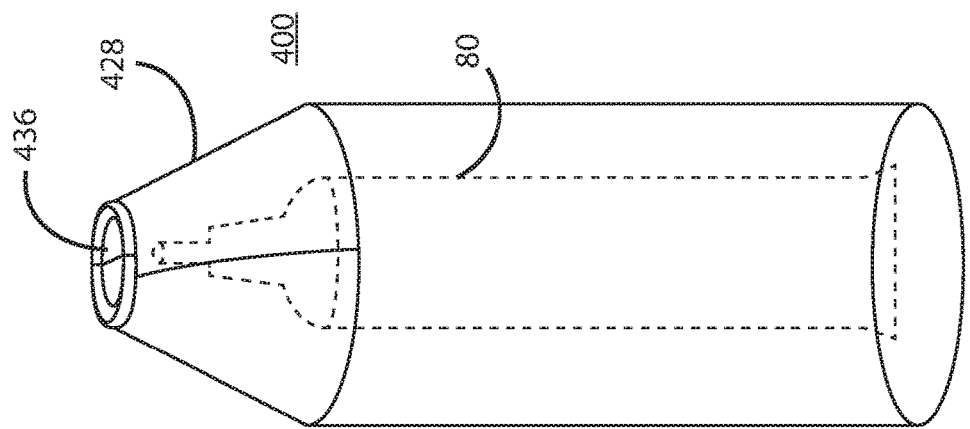
FIGS. 10a-b show perspective views of another exemplary medication accessory for reducing medication non-adherence in two different operable positions.
Figure 10A:
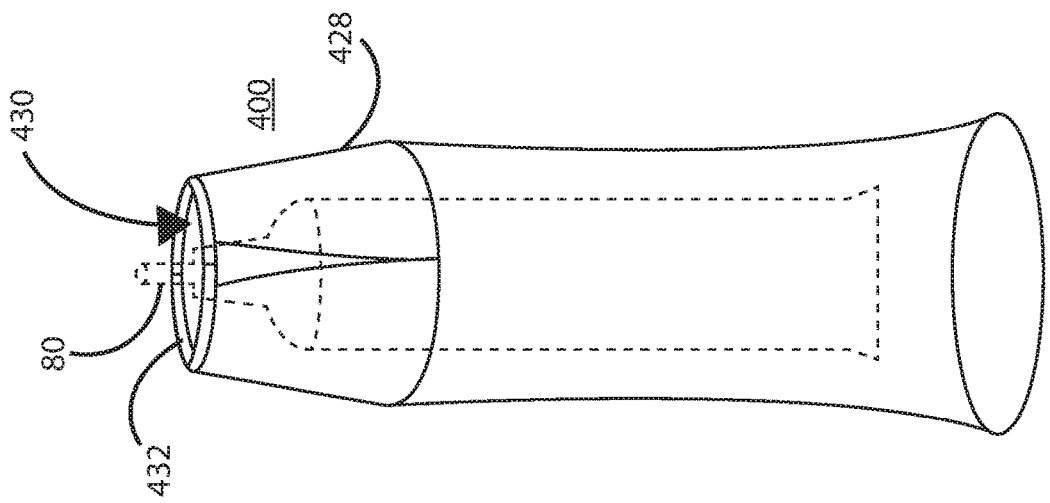

Referring now to FIGS. 10a, 10b and 11, exemplary embodiments for storing other medications are shown. In FIGS. 10a-b, perspective views of another exemplary medication accessory 400 for reducing medication non-adherence is shown in two different operable positions. The accessory 400 may be especially suited for containing pliable medications, such as a squeezable tube 80 for ointments, creams, and the like. Other medication containers also may be housed in the accessory 400.

In the illustrated embodiment, the accessory 400 includes a cover 436 that is closed when no force is applied to the upper portion 428 of the body 420, as shown in FIG. 10a. When a force is applied to the upper portion 428 of the body 420, the cover 436 may open to a biased position that forms an aperture 430 through which the medication 80 may be removed, as illustrated in FIG. 10b.

Referring to FIG. 11, another exemplary medication accessory 500 for reducing medication non-adherence. The accessory 500 may be especially suited for containing rigid medication containers, such as bottles for liquids and the like. Other medication containers also may be housed in the accessory 500. In the illustrated embodiment, the accessory 500 includes a base 56 that may be a rigid component for providing stability to the accessory 500 and a flexible body portion 520 that is pliable to adapt to the rigid body of the medication container. The pliable portion may be made of a textured surface such as rubber or the like to provide frictional contact with the medication container. Other materials and shapes also may be used.

4.0 Exemplary Base Stations 700

Figure 12:
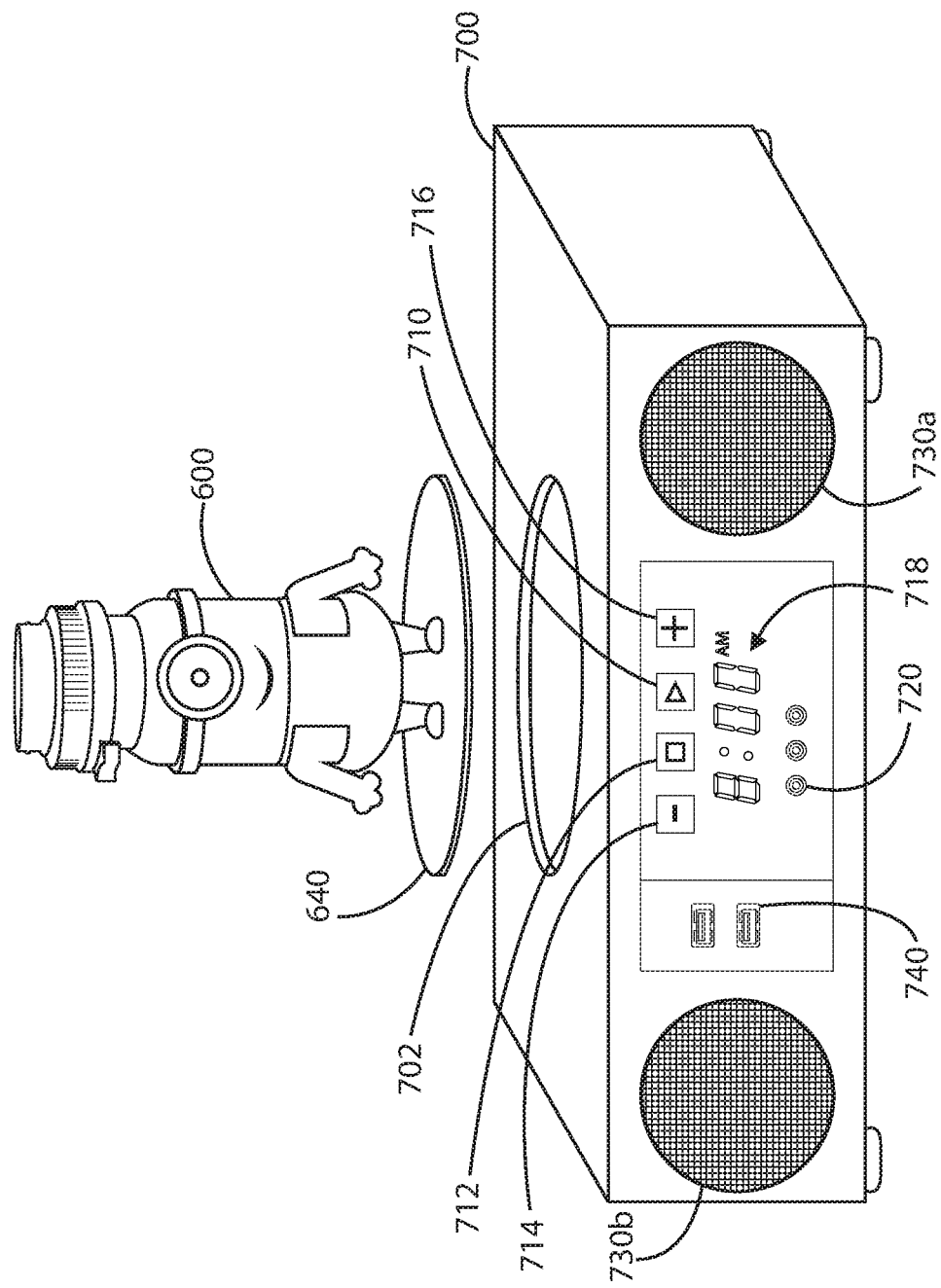
FIG. 12 shows a perspective view of an exemplary base station for use with an exemplary medication accessory for reducing medication non-adherence.

Referring now to FIG. 12, a perspective view of an exemplary base station 700 for use with an exemplary medication accessory 600 for reducing medication non-adherence is shown. The base station 700 may provide a structure for attachment of the medication accessory 600 and also may provide a variety of other functions to increase engagement with a medication user. In the illustrated embodiment, the accessory 600 may include the features described above and also includes a base 640 that engages a slot 702 in the base station 700 to position the accessory 600 to the base station 700. In some embodiments, the slot 640 may provide an arrangement that allows the base 640 to securely engage the slot 702, such as a detent, latch or other mechanism that may be slidably or otherwise engaged by the base 640.

In some embodiments, the base station 700 may be thematically appropriate for a particular aesthetic design 22 of the accessory 600. For example, an accessory having an aesthetic design 22 of a monkey may be combined with a jungle themed base station 700. Similarly, accessory 600 having an esthetic design 22 of a doctor or nurse may be paired with a hospital-themed base station 700. The base station also may include multiple slots 700 to accommodate multiple accessories 600.

In addition, the base station also may provide various other functions to engage the medication user on a regular basis. In this manner, the user is reminded of the medication more frequently than when it is stored in a cabinet or closet and the user is more likely to adhere to the medication protocol. In the illustrated embodiment, the base station 700 may include speakers 730a and 730b as well as playback and volume controls 710, 712, 714 and 716 to provide audio/music playback features. Optional audio ports 720, such as RCA jacks, hdmi ports and the like, also may be provided to enable a variety of audio playback devices to be attached to the base station 700. USB ports 740 also may be provided to enable electrical charging and/or audio playback of devices. The base station 700 also may provide alarm clock features 718 that may allow the user to set alarms for waking up, taking medications, and the like. Other functions also may be provided.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. An accessory for increasing medication adherence in pediatric patients, comprising:
    a body having an aesthetic design, said body made of plastic and having a top surface;
    a circular opening in the top of the body, the circular opening having a diameter;
    an interior wall defining a cylindrical cavity extending downward from the opening and having a substantially closed floor and an upper rim, the cylindrical cavity further having a substantially constant diameter, wherein said upper rim is flush with the top surface of the body;
    wherein the diameter of the opening is substantially equal to the diameter of the cylindrical cavity;
    wherein the cylindrical cavity is adapted to hold a pill bottle selected from the group consisting of a 6 dram pill bottle, a 8 dram pill bottle, a 13 dram pill bottle, a 16 dram pill bottle, a 20 dram pill bottle, a 30 dram pill bottle, and a 40 dram pill bottle,
    wherein the cylindrical cavity has a diameter between about 101% and about 115% of a diameter of said selected pill bottle;
    wherein the cylindrical cavity has a depth between about 80% and about 95% of a height of said selected pill bottle; and
    wherein the cylindrical cavity is adapted to hold said selected pill bottle in an upright position.

2. The accessory of claim 1, where the aesthetic design is a kid-friendly design.

3. The accessory of claim 2, where the kid-friendly design is one selected from the group consisting of a character design, an animal design, or an occupational design.

4. The accessory of claim 1, where the body further includes three-dimensional limbs.

5. The accessory of claim 4, where the three-dimensional limbs comprise at least one selected from the group consisting of legs, arms, hands and feet.

6. The accessory of claim 1, further comprising a cover disposed on the body, wherein the cover is adapted to close the opening and secure the pill bottle in the cavity.

7. The accessory of claim 1, where the interior wall has a textured surface.

8. The accessory of claim 1, further comprising an aperture disposed on a side of the body, wherein the aperture exposes at least a portion of a pill bottle disposed in the cylindrical cavity.

9. The accessory of claim 8, where the aperture is a longitudinal aperture that is substantially vertically disposed, the aperture having a height between about 40% and about 60% of a height of the body and the aperture having a width between about 20% and about 30% of a width of the body.

10. The accessory of claim 1, further comprising a transparent portion disposed on a side of the body, wherein the transparent portion exposes at least a portion of a pill bottle disposed in the cylindrical cavity.

11. The accessory of claim 10, where the transparent portion is longitudinal and substantially vertically disposed, the transparent portion having a height between about 40% and about 60% of a height of the body and the transparent portion having a width between about 20% and about 30% of a width of the body.

12. An accessory for increasing medication adherence in pediatric patients, comprising:
    a body having an aesthetic design, said body made of plastic and having a top surface;
    a circular opening in the top of the body, the circular opening having a diameter;
    an interior wall defining a cylindrical cavity extending downward from the opening and having a substantially closed floor and having an upper rim, the cylindrical cavity further having a substantially constant diameter, wherein said upper rim is flush with the top surface of the body;
    wherein the diameter of the opening is substantially equal to the diameter of the cylindrical cavity;
    wherein the cylindrical cavity has a diameter of between about 2.02 cm and about 2.3 cm and a depth of between about 5.7 cm and about 6.3 cm; and
    wherein the cylindrical cavity is adapted to hold a 6 dram pill bottle in an upright position.

13. The accessory of claim 12, further comprising an aperture disposed on a side of the body, where the aperture exposes at least a portion of a pill bottle disposed in the cylindrical cavity.

14. The accessory of claim 13, where the aperture is a longitudinal aperture that is substantially vertically disposed, the aperture having a height between about 40% and about 60% of a height of the body and the aperture having a width between about 20% and about 30% of a width of the body.

15. The accessory of claim 12, further comprising a transparent portion disposed on a side of the body, where the transparent portion exposes at least a portion of a pill bottle disposed in the cylindrical cavity.

16. The accessory of claim 15, where the transparent portion is longitudinal and substantially vertically disposed, the transparent portion having a height between about 40% and about 60% of a height of the body and the transparent portion having a width between about 20% and about 30% of a width of the body.

17. An accessory for increasing medication adherence in pediatric patients, comprising:
    a body having an aesthetic design, said body made of plastic and having a top surface, where the design further includes three-dimensional limbs, the three-dimensional limbs comprising at least one selected from the group consisting of legs, arms, hands and feet;
    an aperture disposed on the side of the body, where the aperture exposes at least a portion of a pill bottle disposed in the cylindrical cavity, and where the aperture has a height between about 40% and about 60% of a height of the body and the aperture has a width between about 20% and about 30% of a width of the body;
    a circular opening in the top of the body, the circular opening having a diameter;
    an interior wall defining a cylindrical cavity extending downward from the opening and having a substantially closed floor and an upper rim, the cylindrical cavity further having a substantially constant diameter, wherein said upper rim is flush with the top surface of the body; and
    wherein the diameter of the opening is substantially equal to the diameter of the cylindrical cavity;
    wherein the cylindrical cavity is adapted to hold said pill bottle in an upright position, said pill bottle selected from the group consisting of a 6 dram pill bottle, a 8 dram pill bottle, a 13 dram pill bottle, a 16 dram pill bottle, a 20 dram pill bottle, a 30 dram pill bottle, and a 40 dram pill bottle;
    wherein the diameter of the cylindrical cavity is between about 101% and about 115% of a diameter of said selected pill bottle; and
    wherein the cylindrical cavity is between about 80% and about 95% of a height of said selected pill bottle.

\* \* \* \* \*